(12) United States Patent
Singh et al.

(10) Patent No.: US 7,678,927 B2
(45) Date of Patent: Mar. 16, 2010

(54) PROCESS FOR LACTONIZATION IN THE PREPARATION OF STATINS

(75) Inventors: Govind Singh, Noida (IN); Paramvir Bhadwal, Noida (IN); Sanjay Jaiswal, Noida (IN); Dinesh R. Panchasara, Noida (IN); Rajesh Kumar Thaper, Noida (IN); Sushil Kumar Dubey, Noida (IN); Jag Mohan Khanna, Noida (IN)

(73) Assignee: Jubilant Organosys Limited, Noida (IN)

(*) Notice: Subject to any disclaimer, the term of this patent is extended or adjusted under 35 U.S.C. 154(b) by 0 days.

(21) Appl. No.: 11/574,872

(22) PCT Filed: Sep. 8, 2004

(86) PCT No.: PCT/IN2004/000282

§ 371 (c)(1),
(2), (4) Date: Jun. 1, 2007

(87) PCT Pub. No.: WO2006/027790

PCT Pub. Date: Mar. 16, 2006

(65) Prior Publication Data

US 2007/0265457 A1    Nov. 15, 2007

(51) Int. Cl.
*C07D 309/30* (2006.01)
(52) U.S. Cl. .................................................. 549/292
(58) Field of Classification Search ............... 549/292
See application file for complete search history.

(56) References Cited

U.S. PATENT DOCUMENTS

| | | | |
|---|---|---|---|
| 4,444,784 A | 4/1984 | Hoffman et al. | |
| 4,582,915 A | 4/1986 | Sleteinger | |
| 4,820,850 A | 4/1989 | Verhoeven et al. | |
| 4,916,239 A * | 4/1990 | Treiber | 549/292 |
| 5,159,104 A | 10/1992 | Dabora et al. | |
| 5,763,646 A | 6/1998 | Kumar et al. | |
| 5,917,058 A | 6/1999 | Kumar et al. | |
| 6,307,066 B1 | 10/2001 | Murthy et al. | |
| 6,380,401 B1 * | 4/2002 | McManus et al. | 549/292 |
| 6,472,542 B1 * | 10/2002 | Galeazzi et al. | 549/292 |
| 6,562,984 B2 * | 5/2003 | Peters et al. | 549/292 |

OTHER PUBLICATIONS

Dorwald F. A. Side Reactions in Organic Synthesis, 2005, Wiley: VCH, Weinheim p. IX of Preface p. 1-15.*

* cited by examiner

*Primary Examiner*—D. Margaret Seaman
*Assistant Examiner*—Nizal S Chandrakumar
(74) *Attorney, Agent, or Firm*—Workman Nydegger

(57) ABSTRACT

The present invention relates to an improved and industrial friendly process for lactonization to produce compound of the Formula [I], from compound of the Formula [II] in presence of an inorganic compound as a suitable lactonizing agent, preferably alkali metal hydrogen sulfate, and crystallizing the obtained lactone product in a solvent; or treating compound of the Formula [II] in the presence of an inorganic compound preferably alkali metal hydrogen sulfate using phase transfer catalyst in heterogeneous phase followed by crystallizing the obtained lactone product in a solvent.

12 Claims, No Drawings

PROCESS FOR LACTONIZATION IN THE PREPARATION OF STATINS

FIELD OF THE INVENTION

This invention in general relates to a process for producing statins. More particularly, this invention discloses an improved and industrial friendly process for lactonization to produce HMG-CoA reductase inhibitors of the statin class employing suitable lactonizing agent.

BACKGROUND OF THE INVENTION

Lactonization, a well-known process is widely used in the preparation of statins. In this process δ-hydroxy carboxylic acid loses one molecule of water to form an intramolecular ester—a lactone. It is an equilibrium reaction as illustrated in the scheme below and therefore, some means of shifting the equilibrium to the "right" is required to achieve the product in high yield and purity.

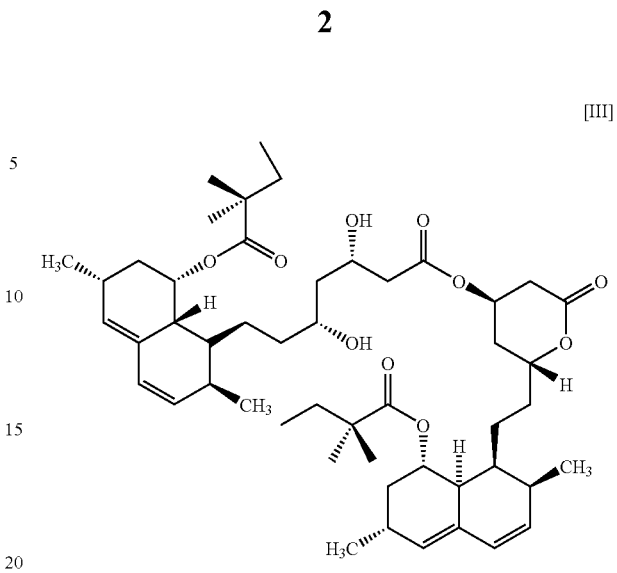

[III]

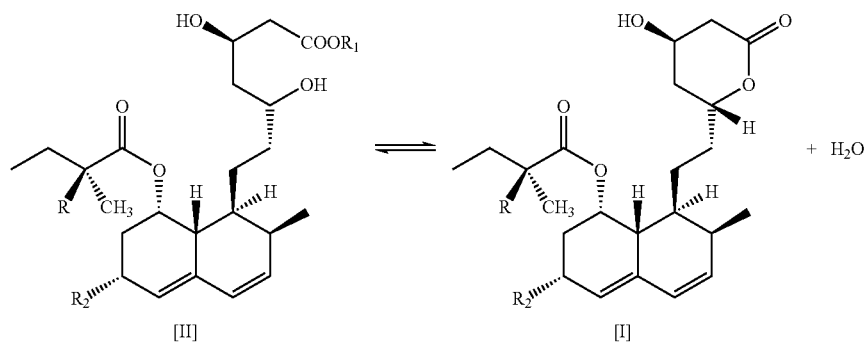

R = H or lower alkyl; $R_1$ = H, metal cation or $NH_4^+$; $R_2$ = H, $CH_3$ or OH Several methods are known in the prior art for lactonization of lovastatin or synthesis of simvastatin. All these methods broadly fall into two categories i.e. thermal dehydration or acid catalysed cyclization.

U.S. Pat. No. 4,444,784 to Hoffman et al., U.S. Pat. No. 4,582,915 to Sleteinger, et al., U.S. Pat. No. 4,820,850 to Verhoeven et al., and U.S. Pat. No. 6,307,066 to Keshava et al., describe the lactonization processes, by heating the statin acid and/or ammonium salt in a suitable solvent such as toluene, butyl acetate, ethyl acetate, cyclohexane to boiling, whereby the azeotropic mixture of the solvent and the water is removed by distillation and the reaction equilibrium is shifted to the formation of the lactone. The process of lactonization at reflux temperatures is complicated by the formation of dimeric impurity of Formula [III]. Moreover, its removal from the product is difficult, thereby affecting the quality of the final lactone product. To minimize dimerization, high dilutions are often used in the lactonization reaction, which is disadvantageous on large-scale manufacturing. Another disadvantage of these processes is that long reaction time is required for completing the reaction, thereby reducing the manufacturing capacity.

U.S. Pat. No. 4,916,239 to Treiber, U.S. Pat. No. 5,917,058 to Kumar et al., and U.S. Pat. No. 5,159,104 to Dabora et al., disclose lactonization processes by treating the open ring hydroxy acid form of the statins preferably in their ammonium salt form in the presence of a strong acid catalyst or a mixture of acid catalyst and water. The resulting lactonized product is isolated after completion of the reaction by the addition of anti-solvent selected from water, hexane, heptane or cyclohexane and the like. The strong acid catalyst used in the process varies from 1.2-1.5 molar equivalents, and is difficult to handle and poses industrially unacceptable disposal problems especially on an industrial scale. The reaction and the subsequent work-up takes about 9-12 hours thereby decreasing the efficiency of the process.

Similarly U.S. Pat. No. 6,562,984 to Peters, et al., describes the lactonization of statin acid or its salt in solvent selected from dichloromethane or acetonitrile under anhydrous reaction conditions in presence of organic or inorganic catalyst with the removal of insoluble hydrated complex formed during the lactonization reaction. However, in this method removal of the insoluble hydrated complex from the reaction mixture and thereafter its disposal reduces the efficiency of the process.

In addition, many of the lactonization methods of the prior art require the use of the strong mineral acid or an organic acid catalyst, thereby making the process hazardous and moreover these corrosive reagents require special care to handle. Furthermore, the generation of large amount of effluent requires special treatment procedures. All these require additional investments thereby increasing the cost of production. In addition, some of the prior art methods describe the lactonization reaction at subzero temperature thereby adding the additional utility costs.

Therefore, there is a need to develop an easy to operate, industrial friendly and yet cost effective process for preparing lactone compounds and still this process should ensure the formation of dimeric impurity to a level less than 0.1%. The present invention addresses these needs.

SUMMARY OF THE INVENTION

It is the principle aspect of the present invention to provide an improved and industrial friendly process for making compound of the Formula [I], employing suitable lactonizing agent, which minimizes the formation of dimeric impurity, generate minimum industrial effluent and the process is cost effective.

In accordance with one preferred embodiment, the present invention provides an improved and industrial friendly process for preparing compound of the Formula [I] from compound of the Formula [II] with an inorganic compound as lactonizing agent, preferably alkali metal hydrogen sulfate followed by crystallizing the resulting lactone product in a suitable solvent, wherein R is hydrogen atom, or a lower alkyl group and $R_1$ is a hydrogen atom, a metal cation or an ammonium cation and $R_2$ is a hydrogen atom, methyl group or a hydroxyl group.

In accordance with another preferred embodiment, the present invention provides an improved and industrial friendly process for preparing compound of the Formula [I] from compound of the Formula [II] with an inorganic compound as lactonizing agent, preferably alkali metal hydrogen sulfate using phase transfer catalyst in heterogeneous phase followed by crystallizing the resulting lactone product in a suitable solvent, wherein R is hydrogen atom, or a lower alkyl group and $R_1$ is a hydrogen atom, a metal cation or an ammonium cation and $R_2$ is a hydrogen atom, methyl group or a hydroxyl group. The reaction is carried out at a temperature not exceeding 50° C. and under inert atmosphere.

DETAILED DESCRIPTION OF THE INVENTION

According to the preferred embodiment of the present invention, there is provided an improved and industrial friendly process for lactonization to prepare compound of the Formula [I] from compound of the Formula [II] in presence of an inorganic compound preferably alkali metal hydrogen sulfate followed by crystallizing the resulting lactone product in a suitable solvent.

The lactonizing agent used herein is an inorganic compound, preferably an alkali metal hydrogen sulfate selected from the group comprising hydrogen sulfate of lithium, sodium and potassium. The amount of the lactonizing agent to be employed may vary depending on the nature of the lactonizing agent and the starting material. Preferably, the amount of the lactonizing agent can be in the range of 2.0-7.0 equivalent against one mole of δ-hydroxy carboxylic acid of statin or analog thereof, more preferably in the range of 2.0-6.0 equivalent.

The solvent employed in the process of the present invention is a water miscible aprotic solvent or a water immiscible aprotic solvent or a mixture thereof. The preferred water miscible aprotic solvents are selected from amides, nitriles, cyclic ethers etc. Preferably the solvent is selected from the group comprising acetonitrile, propionitrile, dimethylsulphoxide, dimethylformamide, dimethylacetamide, tetrahydrofuran, dioxane or mixture thereof. The preferred water immiscible solvents are selected from alkylated esters, acyclic ethers, halogenated solvents, aromatic hydrocarbons etc. Preferably the solvent is selected from the group comprising ethyl acetate, propyl acetate, butyl acetate, methyl propionate, diethyl ether, diisopropyl ether, methyl tertiary butyl ether, dichloromethane, chloroform, carbon tetra chloride, toluene, xylene, anisole or mixture thereof.

According to another embodiment of the present invention there is provided an improved and industrial friendly process for lactonization, to prepare compound of the Formula [I], from compound of the Formula [II] in presence of an inorganic compound preferably alkali metal hydrogen sulfate using phase transfer catalyst in heterogeneous phase followed by crystallizing the resulting lactone product in a suitable solvent.

As disclosed herein, any phase transfer catalyst can be used and is not limited to the examples incorporated herein. The phase transfer catalyst used in the process herein is preferably selected from a group comprising ammonium based phase transfer catalyst, phosphonium based phase transfer catalyst, PEG based phase transfer catalyst, crown ethers etc. Preferably the phase transfer catalyst is selected from tetramethylammonium chloride, triethylbenzylammonium chloride, tetrabutylammonium bromide, tetraethylammonium bromide, tetrabutylammonium hydrogen sulfate, tetrabutylphosphonium chloride, tetrabutylammonium iodide, polyethylene glycol 200, polyethylene glycol 400, polyethylene glycol 600, dibenzo-18-crown-6 and the like. The reaction is performed at a temperature from about ambient to 50° C. under inert atmosphere.

The reaction is performed optionally in the presence of an antioxidant. Suitable antioxidants include butylated hydroxyanisole and butylated hydroxytoluene.

As the lactonizing agent used in the present invention is mild and reaction temperature is low, the potential for forming impurities is low. High Performance Liquid Chromatography reveals that the dimeric impurity is formed in amounts less than 0.1 mass % under these conditions referred to above.

The solvent adopted for the crystallization of the lactone product can be one or a mixture selected from a group comprising water, cyclohexane, heptane or hexane. Choice of anti solvent depends on the type of solvent used in the lactonization reaction. In case reaction is carried out in water miscible solvents like acetonitrile or dimethylformamide the choice of antisolvent is water for the crystallization of lactonized product. On the other hand when lactonization is done in water immiscible solvents of the like, dichloromethane or diisopropyl ether, the choice of antisolvent is less polar solvents i.e. cyclohexane, heptane or hexane which can completely crystallize out the lactonized product in pure form.

The following specific examples illustrate the process of this invention, but they should not be constructed as limiting the scope of the invention.

EXAMPLE 1

Simvastatin ammonium salt (25 g) was taken in acetonitrile (100 ml) under nitrogen atmosphere. To the reaction mixture, potassium hydrogen sulfate (18.7 g) taken in water (50 ml) was added. The reaction mixture was stirred for 3-4 hours at 40-45° C. Water (250 ml) was added to the reaction mixture under stirring. The resulting lactonized product obtained was filtered and washed with water, dried under vacuum to yield crude simvastatin. The crude simvastatin was recrystallized from methanol and water to obtain pure simvastatin.

EXAMPLE 2

Simvastatin ammonium salt (10 g) was taken in dimethylformamide (50 ml) at 20-25° C. To the reaction mixture sodium hydrogen sulfate (10 g), tetra butyl ammonium bromide (0.5 g) and butylated hydroxy anisole (0.01 g) were added. Reaction mixture was stirred at 22-25° C. for 1-2 hours. Reaction mass was filtered and water (150 ml) was added to the filtrate and stirred for one hour. The resulting solid was filtered off and dried under vacuum at 50-55° C. to afford crude simvastatin. The crude simvastatin was recrystallized from methanol and water to obtain pure simvastatin.

Certain modifications and improvements of the disclosed invention will occur to those skilled in the art without departing from the scope of invention, which is limited only by the appended claims.

We claim:

1. An improved lactonization process in the preparation of compound of Formula [I], the process comprising treating the compound of Formula [II] with an alkali metal hydrogen sulfate used as a lactonizing agent in the presence of a phase transfer catalyst,

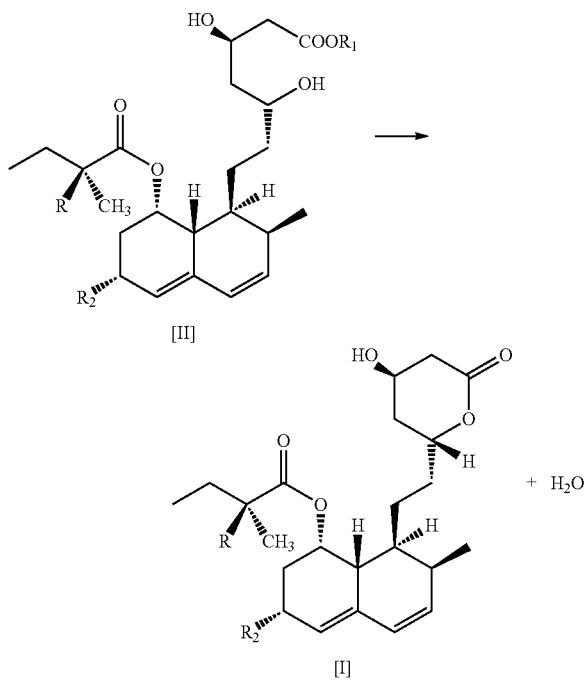

wherein R is a hydrogen atom or a methyl group, $R_1$ is a hydrogen atom or a lithium, sodium, potassium, or an ammonium cation and $R_2$ is a hydrogen atom or a methyl group or a hydroxyl group.

2. The process according to claim 1, wherein the alkali metal hydrogen sulfate is selected from the group comprising hydrogen sulfate of lithium, sodium, potassium or ammonium.

3. The process according to claim 1, wherein the phase transfer catalyst is used in heterogeneous phase.

4. The process according to claim 3, wherein said phase transfer catalyst is selected from the group comprising ammonium based phase transfer catalyst, phosphonium based phase transfer catalyst, PEG based phase transfer catalyst or crown ethers.

5. The process according to claim 1, wherein said lactonization reaction is carried out at a temperature not exceeding 50° C.

6. The process according to claim 1, wherein said lactonization reaction is carried out in presence of water miscible aprotic solvent or water immiscible solvent or a mixture thereof.

7. The process according to claim 6, wherein the water miscible aprotic solvent is selected from amides, nitriles, cyclic ethers or a mixture thereof.

8. The process according to claim 6, wherein the water immiscible solvent is selected from alkylated esters, acyclic ethers, halogenated solvents, aromatic hydrocarbons or a mixture thereof.

9. The process according to claim 7, wherein the water miscible aprotic solvent is selected from the group comprising acetonitrile, propionitrile, dimethylsulphoxide, dimethylformamide, dimethylacetamide, tetrahydrofuran, dioxane or a mixture thereof.

10. The process according to claim 8, wherein the water immiscible solvent is selected from the group comprising ethyl acetate, propyl acetate, butyl acetate, methyl propionate, diethyl ether, diisopropyl ether, methyl tertiary butyl ether, dichloromethane, chloroform, carbon tetra chloride, toluene, xylene, anisole or a mixture thereof.

11. The process according to claim 1, wherein the compound of the Formula [I] is further crystallized from methanol and water.

12. The process as claimed in claim 1, wherein water is used optionally.

* * * * *